(12) United States Patent
Scavone et al.

(10) Patent No.: US 6,197,286 B1
(45) Date of Patent: *Mar. 6, 2001

(54) COSMETIC STICKS CONTAINING TRIGLYCERIDE GELLANTS HAVING IMPROVED HIGH TEMPERATURE TEXTURE AND PHASE STABILITY

(75) Inventors: Timothy Alan Scavone, Loveland; James David Landgrebe, Madeira, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/573,029

(22) Filed: May 17, 2000

(51) Int. Cl.⁷ .............................. A61K 7/32; A61K 7/34; A61K 7/36; A61K 7/38; A61K 7/00
(52) U.S. Cl. ............................ 424/65; 424/66; 424/67; 424/68; 424/400; 424/401
(58) Field of Search .............................. 424/65, 66, 68, 424/59, 400, 401

(56) References Cited

U.S. PATENT DOCUMENTS

| | | | |
|---|---|---|---|
| 4,151,272 | 4/1979 | Geary et al. | 424/68 |
| 5,102,656 | 4/1992 | Kasat | 424/66 |
| 5,156,834 | 10/1992 | Beckmeyer et al. | 424/47 |
| 5,250,291 | 10/1993 | Park et al. | 424/66 |
| 5,449,511 | 9/1995 | Coe | 424/66 |
| 5,500,209 | 3/1996 | Ross et al. | 424/66 |
| 5,516,511 | 5/1996 | Motley et al. | 424/65 |
| 5,650,144 | 7/1997 | Hofrichter et al. | 424/66 |
| 5,718,890 | 2/1998 | Putman et al. | 424/65 |
| 5,744,130 | 4/1998 | Guskey et al. | 424/66 |
| 5,750,096 | 5/1998 | Guskey | 424/65 |
| 5,776,494 | 7/1998 | Guskey et al. | 424/484 |
| 5,833,964 | 11/1998 | Linn et al. | 424/65 |
| 5,840,286 | 11/1998 | Gardlik et al. | 424/65 |
| 5,840,288 | 11/1998 | Guskey et at. | 424/65 |
| 5,885,559 | 3/1999 | Lee et al. | 424/65 |
| 5,965,113 | 10/1999 | Guskey | 424/66 |
| 5,976,514 | 11/1999 | Guskey et al. | 424/65 |

FOREIGN PATENT DOCUMENTS

| | | |
|---|---|---|
| 1 146 867 | 5/1983 | (CA) . |
| 135315 | 4/1995 | (EP) . |
| 2299024A | 9/1996 | (GB) . |
| WO 91/04009 | 4/1991 | (WO) . |
| WO 99/16410 | 4/1999 | (WO) . |
| WO 9951192A2 | 10/1999 | (WO) . |

Primary Examiner—Shelley A. Dodson
(74) Attorney, Agent, or Firm—Lucy Elandjian; William J. Winter

(57) ABSTRACT

Disclosed are anhydrous cosmetic compositions comprising from about 0.01% to about 60% by weight of a cosmetic active; from about 10% to about 90% by weight of a liquid carrier; and from about 1% to about 60% by weight of a solid, polymorphic, unsubstituted, triglyceride gellant characterized by $\beta'$-2 crystalline order within the compositions. These compositions can be formulated as hard sticks, soft solids or creams, and have improved high temperature texture and phase stability and maintain product hardness even after exposure to high and then low storage temperatures.

18 Claims, No Drawings

COSMETIC STICKS CONTAINING TRIGLYCERIDE GELLANTS HAVING IMPROVED HIGH TEMPERATURE TEXTURE AND PHASE STABILITY

TECHNICAL FIELD

The present invention relates to cosmetic stick compositions that are formulated to contain triglyceride gellants in a stabilized crystalline phase characterized by a beta prime-2 (β'-2) crystalline order.

BACKGROUND OF THE INVENTION

There are many types of solid cosmetic sticks that are commercially available or otherwise known in the various arts. These cosmetic sticks include products such as moisturizers, perfumes or fragrances, skin conditioners, antiperspirants, anti-wrinkle products, pharmaceuticals, deodorants, make-up and foundations, sunscreens, and many other products intended for topical application to the skin. Many of these products contain a cosmetic active dispersed within a suitable liquid carrier and contained within a solid gellant or wax matrix that provides the product with sufficient hardness to form a solid stick composition. In addition to providing sufficient product hardness, the solid gellant or wax matrix also acts to contain the liquid carrier and any other liquid ingredients sufficiently to prevent syneresis of such liquids from the product form prior to application.

Wax gellants such as stearyl alcohol and other fatty alcohols are especially common in many commercially available cosmetic stick products. These waxes typically provide a solid matrix within which the cosmetic active and a liquid carrier can be contained with minimal or no liquid syneresis during storage. Other gellants such as the triglyceride gellants have also been used in solid cosmetic sticks, due in large part to the lower raw material cost associated with the use of natural triglycerides.

It has now been found, however, that cosmetic sticks that contain triglyceride gellants can develop stability problems after exposure to high and then low storage temperatures, which can then result in an undesirable softening of and excessive liquid syneresis from the cosmetic stick matrix. It has also been found that triglyceride-based cosmetic stick compositions can be formulated into a more temperature-stable stick form. These compositions are formulated so that exposure to high and then low storage temperatures does not result in excessive softening of the product form and also does not result in excessive development of solvent syneresis during exposure to such temperature changes. It has been found that this can be accomplished by formulating the composition with solid polymorphic triglycerides characterized by beta prime-2 (β'-2) crystalline order within the finished product form. It has been found that by formulating these triglyceride gellants in this manner, that product stability is improved such that product hardness is better maintained and liquid syneresis minimized, especially when exposed to higher and then lower storage temperatures.

It is therefore an object of the present invention to provide a solid cosmetic stick composition that contains a triglyceride gellant and is texture and phase stable when exposed to high and then lower storage temperatures. It is a further object of the present invention to formulate such a composition containing a thermodynamically stable triglyceride gellant, one that is characterized by β'-2 crystalline order within the finished product form.

SUMMARY OF THE INVENTION

The present invention is directed to anhydrous cosmetic stick compositions comprising from about 0.01% to about 60% by weight of a cosmetic active; from about 10% to about 90% by weight of a liquid carrier; and from about 1% to about 60% by weight of a solid, polymorphic, unsubstituted, triglyceride gellant, wherein the triglyceride gellant within the composition is characterized by a β'-2 crystalline order.

It has been found that the cosmetic compositions of the present invention can be formulated for improved texture and phase stability, wherein the product hardness of the compositions is maintained after exposure to high and then low storage temperatures. The improved stability is made possible within the compositions by formulating the triglyceride gellant into a stable crystalline phase that is characterized by β'-2 crystalline order within the finished product form. It has been found that cosmetic stick compositions containing triglyceride gellants tend to soften when exposed to high and then low storage temperatures, and that this can be minimized or avoided by formulating the triglyceride gellant into its β'-2 crystalline order within the finished product form.

DETAILED DESCRIPTION OF THE INVENTION

The cosmetic stick compositions of the present invention comprise as essential ingredients cosmetic active, a liquid carrier, and a defined crystalline form of a polymorphic triglyceride gellant. Each is described in detail hereinafter.

The term "cosmetic stick" as used herein refers generally to any stick composition suitable for topical application to the skin.

The term "anhydrous" as used herein refers to those materials or compositions that contain less than about 5%, more preferably less than about 3%, even more preferably less than about 1%, most preferably zero percent, by weight of free or added water, e.g. water other than the water of hydration typically associated with some solid materials such as particulate antiperspirant active.

The term "solid" as used herein, unless otherwise specified, refers to those materials that are solid at or above 37° C. (skin temperature as measured in the axilla area). The term "liquid" as used herein, unless otherwise specified, refers to those materials that are liquid at or below 37° C. As used herein, a material is determined to be a solid or a liquid at 37° C. by evaluating that material in a finished cosmetic stick composition using Differential Scanning Calorimetry (DSC). For example, A Perkin Elmer Model DSC-7, manufactured by Perkin Elmer Corporation, 761 Main Street, Norwalk Conn., can be used to measure a melting profile of the desired material. This is done by preparing a 20 mg sample in a volatile sample pan arrangement of the desired finished product to be tested. A heating curve (DSC curve) is generated at 5° C. per minute and is analyzed by measuring the partial area that melts below 37° C., and those showing at least 10% of the DSC curve below 37° C. are "liquids" and those showing less than 10% of the DSC curve below 37° C. are "solids."

The term "skin temperature" as used herein refers to the temperature of the axilla or other area of the skin, which is generally at or slightly below a typical body temperature of about 37° C.

The term "ambient conditions" as used herein refers to surrounding conditions under about one (1) atmosphere of pressure, at about 50% relative humidity, and at about 25° C., unless otherwise specified. All values, amounts and measurements described herein are obtained under ambient conditions unless otherwise specified.

The term "volatile" as used herein refers to those materials which have a measurable vapor pressure at 25° C. Such vapor pressures will typically range from about 0.01 mmHg to about 6 mmHg, more typically from about 0.02 mmHg to about 1.5 mmHg, and have an average boiling point at one (1) atmosphere of pressure (atm) of less than about 250° C., more typically less than about 235° C. at one (1) atm. Conversely, the term "non volatile" refers to those materials which are not "volatile" as defined herein.

The cosmetic stick compositions of the present invention can comprise, consist of, or consist essentially of the essential elements and limitations of the invention described herein, as well as any additional or optional ingredients, components, or limitations known or otherwise effective for use in the such compositions.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Product Hardness

The cosmetic stick compositions of the present invention can be formulated as hard sticks, soft solids, creams or other product forms having similar hardness values. The compositions of the present invention therefore have a preferred product hardness of at least about 100 gram·force, typically from about 100 gram·force to about 5,000 gram·force.

For hard stick embodiments, the cosmetic stick compositions preferably have a product hardness value of at least about 600 gram·force, preferably from about 750 gram·force to about 2,000 gram force, more preferably from about 800 gram·force to about 1,400 gram·force. For softer product forms such as soft solids or creams, the cosmetic stick compositions preferably have a product hardness of from about 100 gram·force to about 600 gram·force, preferably from about 120 gram·force to about 500 gram·force, more preferably from about 120 gram·force to about 250 gram·force.

The term "product hardness" or "hardness" as used herein is a reflection of how much force is required to move a penetration cone a specified distance at a controlled rate into a cosmetic stick composition under the following test conditions. Higher values represent harder product and lower values represent softer product. These values are measured at 27° C., 15% relative humidity, using a TA-XT2 Texture Analyzer, available from Texture Technology Corp., Scarsdale, N.Y., U.S.A. The product hardness value as used herein represents the peak force required to move a standard 45° angle penetration cone through the composition for a distance of 10 mm at a rate of 2 mm/second. The standard cone is available from Texture Technology Corp., as part number TA-15, and has a total cone length of about 24.7 mm, angled cone length of about 18.3 mm, a maximum diameter of the angled surface of the cone of about 15.5 mm. The cone is a smooth, stainless steel construction and weighs about 17.8 grams.

Cosmetic Actives

The cosmetic stick compositions of the present invention comprise from about 0.01% to about 60% by weight of a cosmetic active. Suitable actives include any known or otherwise effective cosmetic active that is compatible with the essential ingredients of the cosmetic sticks of the present invention, or which do not otherwise unduly impair the product performance thereof.

Cosmetic actives suitable for use in the compositions of the present invention include moisturizers, emollients, perfumes or fragrances, skin conditioners, antiperspirants, antioxidants, vitamins, anti-wrinkle products, surfactants, pharmaceuticals, deodorants, pigments or colorants, sunscreens or other photo protectants, and any other material intended or otherwise suitable for topical application to the skin.

Non-limiting examples of cosmetic actives suitable for use herein are described in U.S. Pat. No. 6,001,377 (SaNogueira, Jr. et al.), U.S. Pat. No. 6,024,942 (Tanner et al.), U.S. Pat. No. 6,013,271 (Doughty et al.), and U.S. Pat. No. 6,013,270 (Hargraves et al.), U.S. Pat. No. 6,013,248 (Luebbe et al.) U.S. Pat. No. 5,976,514 (Guskey et al.), which descriptions are hereby incorporated herein by reference.

Specific examples of cosmetic actives suitable for use herein include antiperspirant and deodorant actives as described herein, perfumes and frangrances, antimicrobials (antibacterial, antifungal), steroidal anti-inflammatory materials (e.g., hydrocortisone), non-steroidal anti-inflammatory materials, vitamins and derivatives thereof (e.g., thiamin, riboflavin, niacin, pyridoxine, vitamin A, vitamin D, vitamin E, vitamin K), hydroxy and alpha-hydroxy acids (e.g., salicylic acid, citric acid), moisturizers (e.g., silicone and non-silicone), and the like.

Non-limiting embodiments of the cosmetic stick compositions of the present invention include lipsticks, foundations and makeup, antiperspirant and deodorant sticks, suncreen or other photoprotective sticks, emollient sticks, health care actives delivered from a solid stick (e.g., steroidal and non-steroidal anti-inflammatory agents, analgesic stick, etc.), or any other solid stick embodiment from which a desired material, skin active or inert, is incorporated into for topical delivery to the skin.

Antiperspirant and Deodorant Active

The cosmetic compositions of the present invention include antiperspirant and deodorant embodiments which comprise an antiperspirant and/or deodorant active suitable for application to human skin. The active in the composition may be solubilized or in the form of solid particulates or dispersed liquid droplets. The concentration of active in the composition should be sufficient to provide the desired perspiration wetness and/or deodorant control.

The antiperspirant and deodorant embodiments of the present invention preferably comprise antiperspirant active at concentrations ranging from about 0.1% to about 50%, more preferably from about 5% to about 35%, even more preferably from about 7% to about 30%, by weight of the composition. These weight percentages are calculated on an anhydrous metal salt basis exclusive of water and any complexing agents such as glycine, glycine salts, or other complexing agents.

The antiperspirant active for use in the compositions of the present invention include any compound, composition or other material having antiperspirant activity. Preferred antiperspirant actives include astringent metallic salts, especially the inorganic and organic salts of aluminum, zirconium and zinc, as well as mixtures thereof. Particularly preferred are the aluminum-containing and zirconium-containing salts, such as aluminum halides, aluminum chlorohydrate, aluminum hydroxyhalides, zirconyl oxyhalides, zirconyl hydroxyhalides, and mixtures thereof.

Preferred aluminum salts for use in the antiperspirant and deodorant embodiments include those which conform to the formula:

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorohydroxides referred to as "5/6 basic chlorohydroxide", wherein a=5, and "2/3 basic chlorohydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the antiperspirant and deodorant embodiments include those which conform to the formula:

$$ZrO(OH)_{2-a}Cl_a \cdot xH_2O$$

wherein a is from about 1.1 to about 2.0; x is from about 1 to about 8; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorohydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

The antiperspirant and deodorant embodiments of the present invention can also be formulated with deodorant active in addition to or in place of the antiperspirant active described hereinbefore. The term "deodorant active" as used herein includes antimicrobial agents (e.g. bacteriocides, fungicides), malodor-absorbing materials, perfume chemicals that deodorize or mask body odor or which otherwise provide the desired fragrance, or combinations thereof. The concentration of deodorant active can vary with the particular active selected, but preferably ranges from about 0.1% to about 10%, more preferably from about 0.1% to about 5%, by weight of the composition.

Preferred deodorant actives are antimicrobial agents, non-limiting examples of which include cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, phenoxyethanol, and combinations thereof. Most preferred are triclosan and triclocarban.

Triglyceride Gellant

The cosmetic stick compositions of the present invention comprise a solid triglyceride gellant, wherein the solid triglyceride gellant is characterized by β'-2 crystalline order within the composition. Any triglyceride gellant that is known or otherwise effective for use in topical products is suitable for use herein, provided that it can also be formulated to have the requisite crystalline order within the finished product. The concentration of the triglyceride gellant in the composition ranges from about 1% to about 60%, preferably from about 5% to about 30%, even more preferably from about 10% to about 26%, by weight of the composition.

The solid triglyceride gellant for use in the composition must be a solid at or above human skin temperature (37° C.), either inherently or as formulated or processed within the finished composition. The solid triglyceride gellant must also be inherently polymorphic and be capable of being formulated into the composition as a solid matrix that is characterized by β'-2 crystalline order as defined herein. Solid triglyceride gellants that have the above-described characteristics will most typically be unsubstituted triglycerides or mixtures of unsubstituted triglycerides that correspond to the following formula:

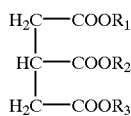

wherein R1, R2 and R3 are the same or different, and are unsubstituted hydrocarbon moieties that are preferably in the form of saturated alkyl groups. These triglycerides will most typically be in the form of triglyceride mixtures wherein R1, R2 and R3 are alkyl groups having from 2 to 30 carbon atoms, and wherein the average number of carbon atoms per alkyl group per triglyceride molecule [(R1+R2+R3)/3] ranges from about 16 to about 24, more preferably from about 18 to about 22.

These solid, unsubstituted, triglyceride gellants are most typically obtained or derived from fully hydrogenated fats such as: (1) vegetable fats and oils such as soybean, corn, sunflower, high erucic acid rapeseed, low erucic acid rapeseed, canola, crambe, meadowfoam, cottonseed, olive, safflower, sunflower, sesame seed, nasturtium seed, tiger seed, ricebran, wallflower, and mustard seed; (2) meat fats such as tallow or lard; (3) marine oils such as menhaden, pilcherd, sardine, whale or herring; (4) nut fats and oils such as coconut, palm, palm kernel, babassu kernel, or peanut, Chinese Vegetable Tallow; (5) milkfat, butterfat; (6) cocoa butter and cocoa butter substitutes such as shea, or illipe butter; (7) structured triglycerides fats made from natural and synthetic routes; and (8) synthetic triglycerides made from hydrocarbon sources.

Specific nonlimiting examples of solid, unsubstituted triglyceride gellants suitable for use herein include tristearin, fully hydrogenated high erucic acid rapeseed oil (e.g., HEAR Oil, CanAmera, Canada), fully hydrogenated CRAMBE oil, and tribehenin (e.g., Syncrowax HR-C, Croda). Most preferred is fully hydrogenated high erucic acid rapeseed oil.

The cosmetic stick compositions may further comprise other gellant materials in addition to and other than the triglyceride gellants described herein, except that at least about 50%, preferably at least about 75%, by weight of the total gellant concentration in the composition must be the triglyceride gellants as described herein.

The triglyceride gellants as formulated within the compositions of the present contain the requisite β'-2 crystalline order, which is a thermodynamically stable crystalline phase which does not readily shift to other crystalline phases over time, even when exposed to higher and then lower storage temperatures. For purposes of defining the compositions of the present invention, the crystalline order of the triglyceride gellant is preferably measured or otherwise characterized at least about 3 months after formulation, preferably at between about 3 and about 6 months after formulation, more preferably at about 6 months after formulation.

The compositions of the present invention remain in the relatively stable β'-2 crystalline phase over periods of time ranging from 0 to about 12 months, preferably from about 3 to about 12 months after formulation, more preferably so that the products remain in the β'-2 crystalline phase over any time interval thereof, e.g. at any time interval between about 3 and about 12 months after formulation. In maintaining their intended crystalline form, these compositions also maintain their product hardness value at the desired level over the time intervals listed above, such that the product hardness for the product preferably does not change by more than about 200 gram·force, more preferably by not more than about 100 gram·force, as measured at 0 and 6 months, more preferably as measured at 3 and 6 months, after formulation.

The triglyceride gellants within the compositions also remain within the stable β'-2 crystalline phase even after exposure to fluctuating storage temperatures. In this context, the fluctuating temperatures refer to typical temperature fluctuations during shipping and storage of the antiperspirant and deodorant compositions between various locations and to different climates, e.g., temperature fluctuations most typically between about −17° C. and about 45° C.

Any known or otherwise effective method of formulating or processing triglyceride solids so that the crystalline phase of the newly formulated or processed triglyceride solid is characterized by β'-2 crystalline order can be applied to the formulation and manufacture of the cosmetic stick compositions of the present invention. Such methods are well known in the edible fat and shortening arts, although it is believed that their reapplication to cosmetic sticks has not heretofore been described. Examples of suitable methods are described in greater detail hereinafter.

X-ray Diffraction Methodology

The triglyceride crystalline phase within the cosmetic stick compositions of the present invention are characterized by β'-2 crystalline order. This type of characterization of triglyceride solids is well known in the chemical and analytical arts, and can be identified by the x-ray diffraction methodology described hereinafter.

It is well known in the analytical and chemical arts that β'-2 crystalline order refers to a particular crystalline phase or crystalline order for most triglyceride materials. Most triglycerides are polymorphic materials that can exist within and shift among several different crystalline phases, including the relatively stable β'-2 crystalline order described herein. In this context, beta prime (β') refers to Orthorhombic crystalline order and can be determined by well known x-ray diffraction methods using short spacing measurements. Methods of characterizing the crystalline order of triglycerides found in high erucic acid rapeseed oil are described in "Polymorphism of 1-Behenoyldistearin and 2-Stearoyldibehenin" by E. S. Lutton and A. J. Fehl; Journal of The American Oil Chemists Society, Vol. 49, No5, PP 336–337 (1972); and "Structural Analogy Between β'Triacylglycerols and n-Alkanes Toward the Crystal Structure Of β'-2 p.p+2.p Triacylglycerols" by Jacco van de Streek, Paul Verwer, Rene de Gelder, and Frank Hollander, JAOCS, Vol. 76, no.11 (1999); which descriptions are incorporated herein by reference.

As used herein, reference to β'-2 crystalline order includes both $β_I'$-2 and $β_{II}'$-2 behenic-stearic-behenic forms of triglycerides in HEAR oil. The β' crytalline order is generally characterized by two or more short spacing reflections in the x-ray powder diagrams around 3.8 and 4.2 angstroms. In the context of β'-2, the "2" refers to the long order characterization of the crystalline phase that is approximately two fatty acid chain lengths long.

The specific characterization of the triglyceride-containing composition of the present invention as being in a β'-2 crystalline phase is determined according to the x-ray diffraction methodology described hereinafter. The following x-ray equipment is used in the diffraction methodology: (1) Philips PW1830 HT Generator w/PW1821 Multi-purpose Sample Stage, (2) Philips PW1397/60 Theta/2-Theta drive and Scintillation Counter, and (3) Philips PW1877 Automated Powder Diffraction Software Program v. 3.5B. Specific instrument parameters are set to divergence slit- 1/4°; scatter slit 1/4°; mask 10 mm; receiving slit 0.05 mm; sample holder 15 mm ×20 mm (Philips p/n PW1172); step size 0.05° 2-theta; start angle 1° 2-theta; end angle 3° 2-theta; time per step 10 sec; anode Cu; generator tension 45 kV; and generator current 40 mA. To characterize short range crystalline order, a scan from start angle 16° 2-theta to an end angle of 26° 2-theta is conducted. The β' crystalline order is characterized as short spacing reflections around 3.8 and 4.2 angstroms.

A external reference standard for use in the methodology is prepared by heating a tribehenin sample (99% tribehenin; Sigma T-7904, Lot# 99H5180) in a 105° C. oven until completely melted. While still molten, the melted tribehenin is then placed in a dewer containing liquid nitrogen until completely solid. The solidified tribehenin is ground to a fine powder using a mortar and pestle. The fine tribehenin powder is placed into a 15 mm×20 mm sample holder (Philips p/n PW1172) and pressed into the holder using a glass microscope slide. All of the excess sample is removed using a knife edge. The holder containing the prepared sample, which is now the external reference standard, is then examined to make sure the surface of the sample is flush with the top of the holder prior to obtaining the x-ray diffraction pattern of the newly prepared external reference standard.

The composition of the present invention, or any other product for evaluation hereunder, is then prepared for x-ray diffraction analysis, and the results of which are then compared to the x-ray diffraction pattern for the external reference standard. The product or composition for analysis is first placed into a 15 mm×20 mm sample holder (Philips p/n PW1172) and then pressed into the holder using a glass microscope slide. The holder is then examined to assure that the sample is flush with the top of the holder prior to obtaining an x-ray diffraction pattern.

X-ray diffraction patterns are obtained for each product sample of interest, and then compared and evaluated relative to the x-ray diffraction pattern of the external reference standard described hereinbefore. The x-ray diffraction patterns are recorded and evaluated for each product sample in terms of peak area and height information by importing the x-ray diffraction patterns of both the external reference standard and the product sample of interest into a BioRad WinIR software package, v. 4.14 Level II, assigning a best fit baseline to the curve(s), integrating the area under the curve(s), and measuring the height of the curve(s), between 1 and 3 degrees 2-theta.

The triglyceride gellant described herein is characterized by β'-2 crystalline order as determined by the x-ray diffraction analysis described herein. The triglyceride gellant, or product containing the triglyceride gellant, is considered for purposes of defining the compositions of the present invention to have the requisite crystalline order when any one or more of the following x-ray diffraction characteristics is noted.

In one embodiment of the cosmetic stick compositions of the present invention, the triglyceride gellant and/or product containing the triglyceride gellant is characterized as having β'-2 crystalline order by an average AUC (area under the curve) at between 1° and 3° 2-theta that is greater than about 8%, preferably greater than greater than about 10%, more preferably greater than about 12%, of the corresponding average AUC for the external reference standard. In this context, the average AUC is determined for the sample product and for the external reference standard from a 10 sample average, each sample being prepared as described herein.

In yet another embodiment of the cosmetic stick compositions of the present invention, the triglyceride gellant and/or product containing the triglyceride gellant is characterized as having β'-2 crystalline order by an average peak height at between 1° and 3° 2-theta of greater than 6%, preferably greater than about 8%, even more preferably greater than about 10%, of the corresponding average peak height of the external reference standard. In this context, the average peak height is determined for the product sample and for the external reference standard from a 10 sample average, each sample being prepared as described above.

It has been found that by formulating these triglyceride-containing compositions into their β'-2 crystalline phase, that product stability is improved such that product hardness is better maintained and liquid syneresis minimized.

Liquid Carrier

The cosmetic stick compositions of the present invention comprises from about 10% to about 95%, preferably from about 20% to about 80%, more preferably from about 30% to about 70%, by weight of an anhydrous liquid carrier suitable for topical application.

The liquid carrier preferably comprises a volatile silicone liquid. The concentration of the volatile silicone ranges from about 10% to about 90%, more preferably from about 15% to about 65%, even more preferably from about 30% to about 60%, by weight of the cosmetic stick composition. The volatile silicone may be a cyclic, linear or branched chain silicone having the requisite volatility as defined herein. Non-limiting examples of suitable volatile silicones are described in Todd et al., "Volatile Silicone Fluids for Cosmetics", Cosmetics and Toiletries, 91:27–32 (1976), which descriptions are incorporated herein by reference. Preferred among these volatile silicones are the cyclic silicones having from about 3 to about 7, more preferably from about 5 to about 6, silicon atoms. Most preferably are those which conform to the formula:

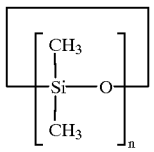

wherein n is from about 3 to about 7, preferably from about 5 to about 6, most preferably 5. These volatile cyclic silicones generally have a viscosity value of less than about 10 centistokes. All viscosity values described herein are measured or determined under ambient conditions, unless otherwise specified. Examples of suitable volatile silicones for use herein include Cyclomethicone D-5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.).

Other suitable liquid carriers include non-volatile silicones. These non-volatile silicone carriers are preferably linear and include those which conform to either of the formulas:

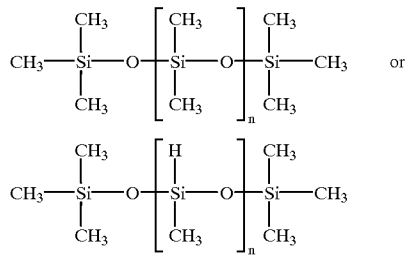

wherein n is sufficiently large to render the material non-volatile. These linear silicone materials will generally have viscosity values of from about 10 centistoke to about 100,000 centistoke, preferably from about 10 to about 500 centistoke, more preferably from about 10 centistoke to about 200 centistoke, even more preferably from about 10 centistoke to about 50 centistoke, as measured under ambient conditions. Examples of non-volatile, linear silicones suitable for use in the cosmetic stick compositions include Dow Corning 200, Dow Corning 225, Dow Corning 1732, Dow Corning 5732, Dow Corning 5750 (available from Dow Corning Corp.); and SF-96, SF-1066 and SF18(350) Silicone Fluids (available from G. E. Silicones).

Other suitable liquid carriers include volatile, nonpolar hydrocarbon liquids. In this context, the term "nonpolar" means that these volatile hydrocarbon liquids have a solubility parameter of less than about 7.5 $(cal/cm^3)^{0.5}$, most typically about 5.0 $(cal/cm^3)^{0.5}$ to about 7.5 $(cal/cm^3)^{0.5}$. These volatile, nonpolar hydrocarbon liquids preferably contain only hydrogen and carbon and therefore preferably contain no functional groups. Solubility parameters as described above are determined by methods well known in the chemical arts for establishing the relative polar character of a solvent or other material. A description of solubility parameters and means for determining them are described by C. D. Vaughan, "Solubility Effects in Product, Package, Penetration and Preservation" 103 Cosmetics and Toiletries 47–69, October 1988; and C. D. Vaughan, "Using Solubility Parameters in Cosmetics Formulation", 36 J. Soc. Cosmetic Chemists 319–333, September/October, 1988, which descriptions are incorporated herein by reference.

The nonpolar, volatile hydrocarbon liquid as a liquid carrier for use in the composition of the present invention is preferably a liquid paraffin and/or isoparaffin having the requisite volatility and nonpolar character. The nonpolar, volatile hydrocarbon liquids can have a cyclic, branched and/or chain configuration, and can be saturated or unsaturated, preferably saturated.

Preferred volatile, nonpolar hydrocarbon liquids are branched chain hydrocarbons having the requisite volatility and solubility parameter, and which have from about 6 to about 40 carbon atoms, preferably from about 6 to about 20 carbon atoms. These preferred hydrocarbon liquids will most typically be formulated as a combination of two or more of the above-described branched chain hydrocarbons, wherein the combination of two or more hydrocarbons have different molecular weights, number of carbon atoms, and/or chain configurations. Specific nonlimiting examples of such combinations include the isoparaffins available from Exxon Chemical Company, Baytown, Tex. U.S.A, sold as Isopar M (C13-C14 Isoparaffin), Isopar C (C7-C8 Isoparaffin), Isopar E (C8-C9 Isoparaffin), Isopar G (C 10-11 Isoparaffin), Isopar L (C11-C13 Isoparaffin), Isopar H (C11-C12 Isoparaffin), and combinations thereof. Other nonlimiting examples of suitable branched chain hydrocarbons include Permethyl 99A (C12, isododecane), Permethyl 101A (C16, isohexadecane), Permethyl 102A (C20, isoeicosane), and combinations thereof. The Permethyl series are available from Presperse, Inc., South Plainfield, N.J., U.S.A. Other nonlimiting examples of suitable branched chain hydrocarbons include petroleum distallates such as those available from Phillips Chemical as Soltrol 130, Soltrol 150, Soltrol 170, and those available from Shell as Shell Sol-70, -71, and -2033.

Still other suitable isoparaffins include C9-C11 Isoparaffin, C9-C13 Isoparaffin, C9-C14 Isoparaffin, C10-C13 Isoparaffin, C12-C14 Isoparaffin, C13-C16 Isoparaffin, C14-C18 Isoparaffin, and hydrogenated polyisobutene available from Amoco as the Panalane Series and from Fanning Corporation as the Fancor P series.

Nonlimiting examples of other volatile, nonpolar hydrocarbon liquids suitable for use in the cosmetic stick compositions include paraffins such as dodecane, octane, decane and combinations thereof, and the Norpar series of paraffins available from Exxon Chemical Company such as Norpar-12, -13, and -15 and the Neosolve series of paraffins available from Shell. Yet another example includes C11-C 15 alkanes/cycloalkanes, such as those available from Exxon as Exxsol D80.

Other suitable liquid carriers for use in the cosmetic stick compositions of the present invention include any liquid material suitable for use on human skin which is also compatible within the cosmetic stick formulation selected. Examples of some of the many suitable liquid carriers are described in Cosmetics, Science, and Technology, Vol. 1, 27–104, edited by Balsam and Sagarin (1972); U.S. Pat. No. 4,202,879 issued to Shelton on May 13, 1980; and U.S. Pat. No. 4,816,261 issued to Luebbe et al. on Mar. 28, 1989, which descriptions are incorporated herein by reference.

Optional Ingredients

The cosmetic stick compositions of the present invention may further comprise any optional materials that are known for use in cosmetic or other personal care products, or which are otherwise suitable for topical application to human skin.

Nonlimiting examples of such other optional materials include emulsifiers, distributing agents, residue masking agents, inert fillers, preservatives, processing aides such as viscosity modifiers, wash-off aids, and so forth. Other suitable optional materials include other solid gellants or waxes in addition to and other than the solid triglyceride gellants described herein. Examples of such optional materials are described in U.S. Pat. No. 4,049,792 (Elsnau); U.S. Pat. No. 5,019,375 (Tanner et al.); and U.S. Pat. No. 5,965,113 (Guskey), which descriptions are incorporated herein by reference.

Methods of Manufacture

The cosmetic stick compositions of the present invention may be prepared by any known or otherwise effective technique, suitable for providing a cosmetic stick composition having the product characteristics described herein, provided that the method also includes control over the crystalline phase of the triglyceride gellant so that the triglyceride gellant as formulated into or formed within the composition is characterized by the $\beta'$-2 crystalline order as described herein.

Generally, the triglyceride-containing compositions herein can be prepared by controlling or slowing the phase transition of the triglyceride during formulation as described below and then following this with a heat tempering process stage, if necessary, wherein the formulated triglyceride-containing composition comes out of a cooling tunnel stage in the $\beta'$-0 crystalline phase (i.e. free of long range crystalline order) and then is tempered at 40–45° C. for 3–7 days to induce the transition to the $\beta'$-2 phase. Alternate processing methods include manipulating process cooling temperatures and cooling tunnel conditions to induce the transition to the $\beta'$-2 phase. In addition, a reheat scraped surface heat exchanger step in the process immediately following the cooling heat exchanger may be introduced to accelerate transition to the $\beta'$-2 phase. Finally, seed crystallization in the $\beta'$-2 phase may be introduced as another method to accelerate transition to the $\beta'$-2 phase.

The cosmetic stick compositions of the present invention have a Percent Delta Texture Value (% DTV) of less than about 15%, which means that the texture and phase stability of the compositions remains substanstially stable even when exposed to higher and then lower storage temperatures. In this context, % DTV (and therefore texture stability) is measured by placing product at 21° C. and other identical product at 45° C. Each of the products are maintained at their designated and respective temperatures for 7 days, and then immediately afterward kept at 21° C. for 7 more days, immediately after which product hardness for each product is measured and the following texture values calculated: (1) Delta Texture Value (DTV)=Texture Value At 21° C.−Texture Value At 45° C. returned to 21° C.; and % DTV=100×DTV/Texture Value at 21° C.

One method of controlling the triglyceride crystalline or molecular phase distribution in a product composition is by controlling the rate of cooling of the liquefied triglyceride solid during formulation so that the mean DSC (Differential Scanning Calorimetry) for the resulting triglyceride phase in the formulation is between about 60° C. and about 65° C. and the resulting triglyceride gellant in the formulation is in the $\beta'$-2 phase as determined by the x-ray phase methodology described herein. Methods for determining DSC values for solid materials are well known in the chemical arts, and can be easily applied in the present development. As an example, a Perkin Elmer model DSC-7 manufactured by Perkin Elmer Corporation, 761 Main Street, Norwalk Conn., can be used to measure a melting profile of the desired material This is done by preparing a 20 mg sample in a volatile sample pan arrangement of the desired finished product to be tested. The heating curve (DSC curve) is generated at 5° C. per minute.

The antiperspirant and deodorant stick embodiments, for example, can be formulated by mixing the carrier liquid(s) under ambient conditions, or under conditions sufficient to render the admixture fluid or liquid, and adding the triglyceride and other non-active solids to the mixture and then heating the resulting mixture sufficiently to liquefy the added materials and to form a single phase liquid, e.g. 85° C. Antiperspirant or other similar solid cosmetic solid, if any, are then added to and dispersed throughout the heated, single phase liquid before allowing the resulting combination to cool to approximately 78° C., at which point perfumes or other similar materials are mixed into the combination, which is then allowed to cool to about 60° C. which is just above the solidification temperature of the formulation matrix at a cooling rate of from 0.5° C. to 200° C. per minute (rate selected to isolate the triglyceride gellant in its β'-2 crystalline phase) before being poured into dispensing packages and allowed to solidify under ambient conditions, after which the product is tempered at 40° C. to 45° C. to convert the product if necessary to its β'-2 crystalline order.

The present invention, therefore, is also directed to methods of making the cosmetic compositions of the present invention, wherein the compositions are made by any method which controls solid triglyceride crystallization to the desired end results described herein. The cosmetic stick embodiments of the present invention may then be applied topically to the desired area of the skin in an amount effective to provide the desired result.

EXAMPLES

The following non-limiting examples illustrate specific embodiments of the cosmetic stick compositions of the present invention. Each is prepared in a similar manner, with modifications made to accommodate the various ingredients and product forms, but generally each is formulated by combining the solid gellants and liquid carriers in a vessel equipped with a heat source. The combined solids and liquids are heated to a temperature ranging from 85° C. to 96° C. and agitated to dissolve the solid gellants until the mixture forms a homogeneous clear to slightly cloudy solution, at which point any solid cosmetic active is added to and dispersed throughout the heated solution while maintaining mixing. The resulting heated combination is then circulated through a scraped wall heat exchanger and cooled to 62° C. before filling the cooled mixture into plastic dispensing canisters and allowed to cool and solidify within the canisters over a 20 minute period (cooling rate of 2° C./min) through a forced air cooling tunnel having an air temperature of 21° C. The exemplified compositions are then placed in a constant temperature tempering room maintained at 45° C. for a period of one week (7 days) after which they are withdrawn and returned to room temperature where they are evaluated for hardness and by X-ray crystallography for phase properties according to the method described herein.

Each of the exemplified compositions contain a solid triglyceride crystalline matrix that is in the β'-2 phase. Each of the exemplified compositions is applied topically to the appropriate area of the skin, in accordance with the methods of use described herein.

All exemplified amounts are weight percentages based upon the total weight of the cosmetic stick composition, unless otherwise specified.

TABLE 1

| Ingredient | Example 1 | Example 2 | Example 3 | Example 4 | Example 5 |
|---|---|---|---|---|---|
| Al Zr Trichlorhydrex Glycinate | 25.00 | 25.00 | 20.00 | 26.00 | 25.25 |
| Cyclopentasiloxane | 37.375 | 34.25 | 42.375 | 39.25 | 59.625 |
| Tribehenin (Syncrowax HR-C)[1] | 0.00 | 0.00 | 17.5 | 20.00 | 7.50 |
| C18–36 Acid Triglyceride (Syncrowax HGLC)[2] | 4.375 | 5.00 | 4.375 | 5.00 | 1.875 |
| Perfume | 0.75 | 0.75 | 0.75 | 0.75 | 0.75 |
| C13–14 Isoparaffin (Isopar M)[3] | 10.00 | 10.00 | 10.00 | 10.00 | 0 |
| Dimethicone 50 cs | 5.00 | 5.00 | 5.00 | 5.00 | 5.00 |
| Fully Hydrogenated HEAR Oil[4] | 17.5 | 20.00 | 0.00 | 0.00 | 0 |
| Totals | 100.00 | 100.00 | 100.00 | 100.00 | 100.00 |
| Product hardness (gram · force) | 885 | 1400 | 725 | 1185 | 230 |
| % DTV | 5% | 3% | 8% | 6% | 4% |

[1]Croda, Inc., New York, New York, USA
[2]Croda, Inc., New York, New York, USA
[3]Exxon Chemical Company, Baytown, Texas, USA,
[4]CanAmera, Canada

TABLE 2

Analgesic Stick

| Ingredient | Weight % |
|---|---|
| Methyl Salicylate | 20.00 |
| Menthol | 10.00 |
| PAO 3004 | 45.00 |
| Fully Hydrogenated HEAR oil | 20.00 |
| Syncrowax HGLC | 5.00 |

TABLE 3

Moisturizing Emollient Stick

| Ingredient | Weight % |
|---|---|
| Tocopherol Acetate | 1.00 |
| Petrolatum | 20.00 |
| PAO 3004 | 58.95 |
| Fully Hydrogenated HEAR oil | 15.00 |
| Syncrowax HGLC | 5.00 |
| Propyl Paraben | 0.00 |

TABLE 4

Sunscreen Stick

| Ingredient | Weight % |
|---|---|
| Cyclomethicone | 20.00 |
| Octylmethoxycinnamate | 7.50 |
| PAO 3004 | 34.50 |
| Fully Hydrogenated HEAR oil | 25.00 |
| Syncrowax HGLC | 5.00 |
| Benzophenone-3 | 3.00 |
| Octyl Salicylate | 5.00 |

TABLE 5

Cosmetic Stick

| Ingredient | Weight % |
| --- | --- |
| Cyclomethicone | 45.00% |
| Dimethicone | 20.00% |
| Zinc Oxide | 5.00% |
| Fully Hydrogenated HEAR oil | 25.00% |
| Syncrowax HGLC | 5.00% |

What is claimed is:

1. Anhydrous cosmetic stick compositions comprising:
   (a) from about 0.01% to about 60% by weight of a cosmetic active;
   (b) from about 10% to about 90% by weight of a liquid carrier;
   (c) from about 1% to about 60% by weight of a solid, polymorphic, unsubstituted, triglyceride gellant,
   wherein the composition is anhydrous and the triglyceride gellant within the composition is characterized by a β'-2 crystalline order.

2. The compositions of claim 1 wherein the stick compositions have a product hardness of at least about 600 gram·force.

3. The compositions of claim 1 wherein the stick compositions have a product hardness of from about 100 gram·force to about 600 gram·force.

4. The composition of claim 1 wherein the composition contains less than about 1% by weight of free water.

5. The compositions of claim 1 wherein the triglyceride gellant comprises a solid triglyercide corresponding to the formula:

$$\begin{array}{l} H_2C-COOR_1 \\ \phantom{H_2}| \\ HC-COOR_2 \\ \phantom{H_2}| \\ H_2C-COOR_3 \end{array}$$

wherein R1, R2 and R3 are independently selected from saturated alkyl groups having from about 2 to about 30 carbon atoms, and wherein the average number of carbon atoms per saturated alkyl group as represented by the expression (R1+R2+R3)/3 is from about 16 to about 24.

6. The composition of claim 1 wherein the composition comprises from about 5% to about 30% by weight of the solid polymorphic triglyceride gellant.

7. The composition of claim 1 wherein the cosmetic active is selected from the group consisting of antiperspirants, perfumes, moisturizers, emollients, anti-oxidants, vitamins, surfactants, pharmaceuticals, deodorants, sunscreens, and combinations thereof.

8. The composition of claim 7 wherein the cosmetic active is an antiperspirant active selected from the group consisting of aluminum-containing active, zirconium-containing active, and combinations thereof.

9. The composition of claim 8 wherein the antiperspirant active within the composition is in the form of solid particulates.

10. The composition of claim 1 wherein the triglyceride gellant is selected from the group consisting of tristearin, fully hydrogenated high erucic acid rapeseed oil, hydrogenated low erucic acid rapeseed oil, CAMBE Oil, tribehenin, and combinations thereof.

11. The composition of claim 10 wherein the triglyceride gellant is fully hydrogenated high erucic acid rapeseed oil.

12. The composition of claim 1 wherein the % Delta Texture Value of less than about 15%.

13. The composition of claim 1 wherein the triglyceride gellant represents at least about 50% by weight of the total gellant concentration in the composition.

14. The composition of claim 1 wherein the liquid carrier comprises a volatile, nonpolar hydrocarbon liquid.

15. The composition of claim 1 wherein the composition contains less than 3% by weight of free or added water.

16. The composition of claim 1 wherein the composition at 6 months after formulation provides an x-ray diffraction pattern according to the X-ray Diffraction Methodology, wherein the pattern is characterized by an average area under the curve at between 1° and 3° 2-theta of greater than about 12% of the corresponding average area under the curve for a 99% tribehenin external reference standard.

17. The composition of claim 1 wherein the composition at 6 months after formulation provides an x-ray diffraction pattern according to the X-ray Diffraction Methodology, wherein the pattern is characterized by an average peak height at between 1° and 3° 2-theta of greater than about 10% of the corresponding average peak height of a 99% tribehenin external reference standard.

18. A method of stabilizing cosmetic stick compositions containing solid, polymorphic, unsubstituted triglyceride gellants, wherein the method comprises formulating the cosmetic stick compositions with a triglyceride gellant so that the within the composition is characterized by β'-2 crystalline order.

* * * * *